United States Patent [19]

Weinberger et al.

[11] Patent Number: 5,764,723
[45] Date of Patent: Jun. 9, 1998

[54] APPARATUS AND METHOD TO GATE A SOURCE FOR RADIATION THERAPY

[75] Inventors: Judah Z. Weinberger, Teaneck, N.J.; Howard I. Amols, New York; Peter B. Schiff, Larchmont, both of N.Y.

[73] Assignee: The Trustees of Columbia University in the City of New York, New York, N.Y.

[21] Appl. No.: 730,965

[22] Filed: Oct. 16, 1996

[51] Int. Cl.$^6$ .................................................. A61N 5/10
[52] U.S. Cl. ................................................ 378/65; 378/95
[58] Field of Search ............................. 378/64, 65, 68, 378/69, 95

[56] References Cited

U.S. PATENT DOCUMENTS

| | | | |
|---|---|---|---|
| 2,967,944 | 1/1961 | Lusted | 250/95 |
| 3,520,295 | 7/1970 | Kelly | 128/2.06 |
| 3,524,058 | 8/1970 | Robertson et al. | 250/65 |
| 3,626,932 | 12/1971 | Becker | 128/2.06 |
| 3,871,360 | 3/1975 | Van Horn et al. | 378/95 X |
| 4,031,884 | 6/1977 | Henzel | 378/95 X |
| 4,994,965 | 2/1991 | Crawford et al. | 378/95 |

*Primary Examiner*—David P. Porta
*Attorney, Agent, or Firm*—John P. White; Cooper & Dunham LLP

[57] ABSTRACT

A radiation therapy apparatus and method for applying radiation to a patient in synchronism with one of a plurality of states of a cardiac cycle of the patient and one of a plurality of states of a respiratory cycle of the patient. An electrocardiograph is operatively connected to the patient and a respiratory monitor is operatively connected to the patient. A controller is provided for receiving an output from said electrocardiograph indicative of which of said plurality of cardiac cycle states the cardiac cycle is presently in and for receiving an output from said respiratory monitor indicative of which of said plurality of respiratory cycle states said respiratory cycle is presently in. A radiation applicator applies radiation to the patient in response to a trigger signal from the controller, said trigger signal being generated by said controller in response to said output from said electrocardiograph and said output from said respiratory monitor.

20 Claims, 4 Drawing Sheets

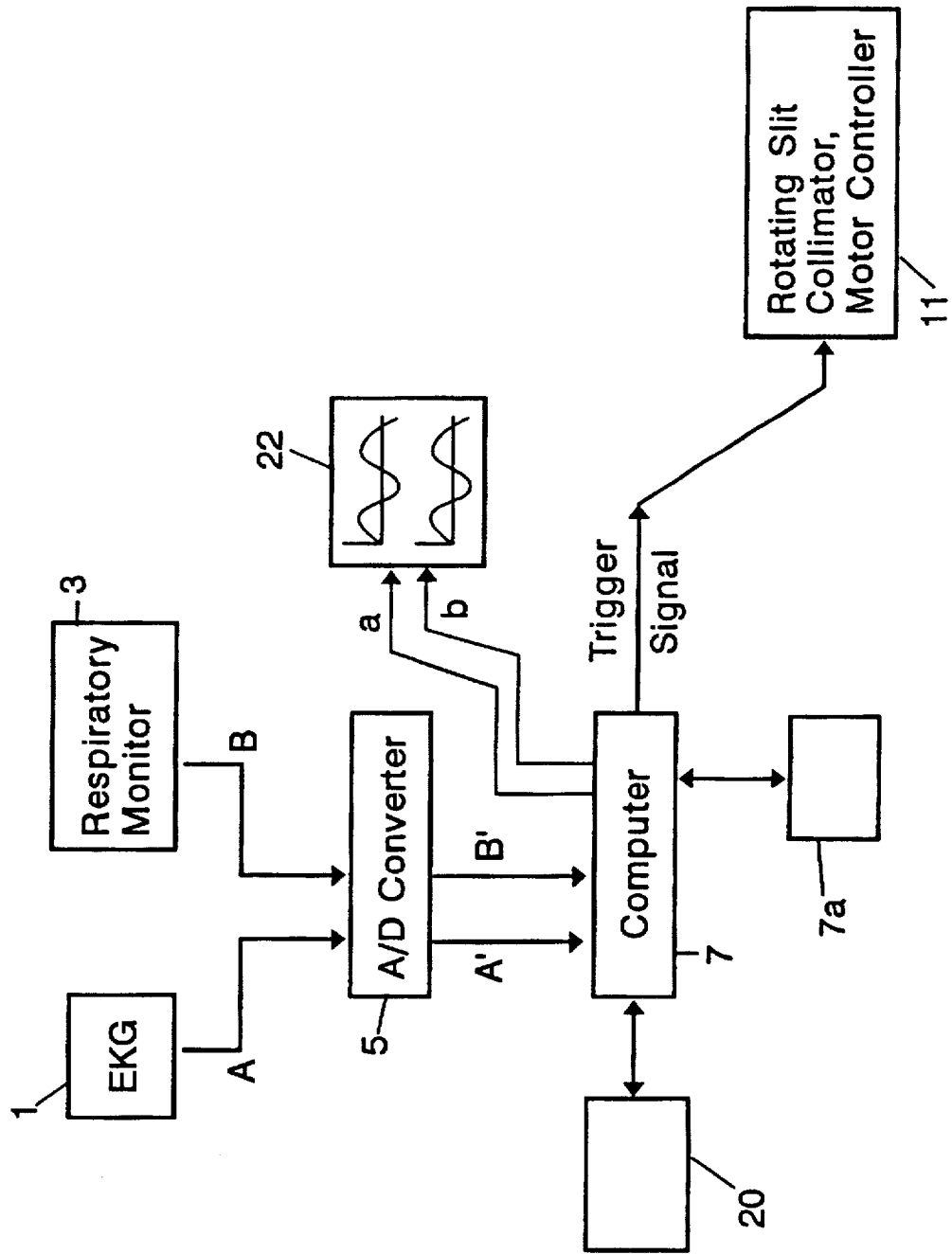

5,764,723

APPARATUS AND METHOD TO GATE A SOURCE FOR RADIATION THERAPY

BACKGROUND OF THE INVENTION

The present invention relates to an apparatus and a method to gate a source for radiation therapy. More particularly, the present invention relates to an apparatus and a method to gate an x-ray source for radiation therapy. The radiation may be directed to target sites that move with or are affected by the cardiac and/or respiratory cycles. Such sites include, but are not limited to, the heart, the mediastinum, the lung, the breast, the kidney, the esophagus, the chest area, the liver, and the peripheral blood vessels. Tumors at these listed sites, as well as other sites, may be treated.

Throughout this application various publications are referenced by Arabic numerals within parentheses. Full citations for these references may be found at the end of the specification immediately preceding the claims. The disclosures of all of these publications in their entireties are hereby incorporated by reference into this application in order to more fully describe the state of the art to which this invention pertains.

Ionizing radiation delivered to coronary arteries before, during, and/or after balloon angioplasty has been shown to reduce the proliferation of smooth muscle cells and neointomia formation, thereby inhibiting restenosis. (1–5) To date, most work in this field has utilized temporary intraluminal insertion of high activity beta or gamma seed, wires, or fluids to deliver radiation. The treatment of restenosis is an important clinical problem in that 400,000 plus procedures are performed annually in the United States, at a total cost of approximately $5 billion. The resulting restenosis rate is about 30–40%.

In any case, the insertion of radioactive sources into coronary arteries presents problems including radiation safety issues and possible excess exposure to patients and staff; possible inhomogeneous dose distributions; and possible thrombus formation and/or embolization of the radioactive source in the arterial tree.

External beam irradiation has been proposed for the treatment of coronary arteries. (6–9) More generally, the application to a patient of such externally produced radiation and the problems associated therewith have been discussed. (10–25) In any case, conventional external beam radiation application suffers from the disadvantage that coronary motion during treatment would necessitate the application of a radiation field of large size that would affect an unacceptably large volume of normal tissue surrounding the targeted treatment volume.

As an alternative, treatments could be fractionated to reduce normal tissue damage. However, such fractionation raises the additional complications of target localization and treatment reproducibility, as coronary arteries cannot be easily visualized on standard radiation oncology type simulation films or portal images.

SUMMARY OF THE INVENTION

It is an object of the present invention to provide an apparatus and method in which the application of radiation from a linear accelerator or other radiation production source is synchronized with the occurrence of predetermined events in a patient's cardiac and respiratory cycles. This enables treatment with smaller field sizes and reduces normal tissue complications.

According to one aspect of the present invention, a radiation therapy apparatus for applying radiation to a patient in synchronism with one of a plurality of states of a cardiac cycle of a patient and one of a plurality of states of a respiratory cycle of a patient is provided, comprising an electrocardiograph operatively connected to the patient, a respiratory monitor operatively connected to the patient, control means for receiving an output from said electrocardiograph indicative of which of said plurality of cardiac cycle states the cardiac cycle is presently in and for receiving an output from said respiratory monitor indicative of which of said plurality of respiratory cycle states said respiratory cycle is presently in, and radiation application means for applying radiation to the patient in response to a trigger signal from said control means, said trigger signal being generated by said control means in response to said output from said electrocardiograph and said output from said respiratory monitor.

According to another aspect of the instant invention a radiation therapy apparatus for applying radiation to a patient in synchronism with one of a plurality of states of a cardiac cycle of a patient and one of a plurality of states of a respiratory cycle of a patient is provided, comprising an electrocardiograph operatively connected to the patient, a respiratory monitor operatively connected to the patient, display means for receiving an output from said electrocardiograph for displaying which of said plurality of cardiac cycle states the cardiac cycle was in at a given time and for receiving an output of said respiratory monitor for displaying which of said plurality of respiratory cycle states said respiratory cycle was in at a given time, control means for receiving user input indicative of a selected point or interval of time when a chosen one of said plurality of cardiac cycle states overlaps with a chosen one of said plurality of respiratory states and for outputting a trigger signal at said selected point or interval of time based upon the output from the electrocardiograph input thereto and the output from the respiratory monitor input thereto, and radiation application means for applying radiation to the patient in response to the trigger signal from said control means.

According to another aspect of the instant invention a method of applying radiation to a patient in synchronism with one of a plurality of states of a cardiac cycle of a patient and one of a plurality of states of a respiratory cycle of a patient is provided, comprising operatively connecting an electrocardiograph to the patient, operatively connecting a respiratory monitor to the patient, receiving, at a control means, an output from said electrocardiograph indicative of which of said plurality of cardiac cycle states the cardiac cycle is presently in and for receiving, at the control means, an output from said respiratory monitor indicative of which of said plurality of respiratory cycle states said respiratory cycle is presently in, and applying radiation to the patient in response to a trigger signal from said control means, said trigger signal being generated by said control means in response to said output from said electrocardiograph and said output from said respiratory monitor.

According to another aspect of the instant invention a method of applying radiation to a patient in synchronism with one of a plurality of states of a cardiac cycle of a patient and one of a plurality of states of a respiratory cycle of a patient is provided, comprising operatively connecting an electrocardiograph to the patient, operatively connecting a respiratory monitor to the patient, displaying, on a display means, an output from said electrocardiograph indicative of which of said plurality of cardiac cycle states the cardiac cycle was in at a given time, displaying, on the display means, an output from said respiratory monitor indicative of which of said plurality of respiratory cycle states said respiratory cycle was in at a given time, receiving, at a control means, user input indicative of a selected point or interval of time when a chosen one of said plurality of cardiac cycle states overlaps with a chosen one of said plurality of respiratory cycle states, outputting a trigger signal from the control means at said selected point or interval of time based upon the output from the electrocardiograph input to the control means and the output from the respiratory monitor input to the control means, and applying radiation to the patient in response to the trigger signal from said control means.

These and other advantages will become apparent from the detailed description, accompanying claims, and attached drawing figures.

BRIEF DESCRIPTION OF THE DRAWINGS

FIG. 4 shows a block diagram of a fourth embodiment of the instant invention.

DETAILED DESCRIPTION OF THE DRAWINGS

Figure 1:
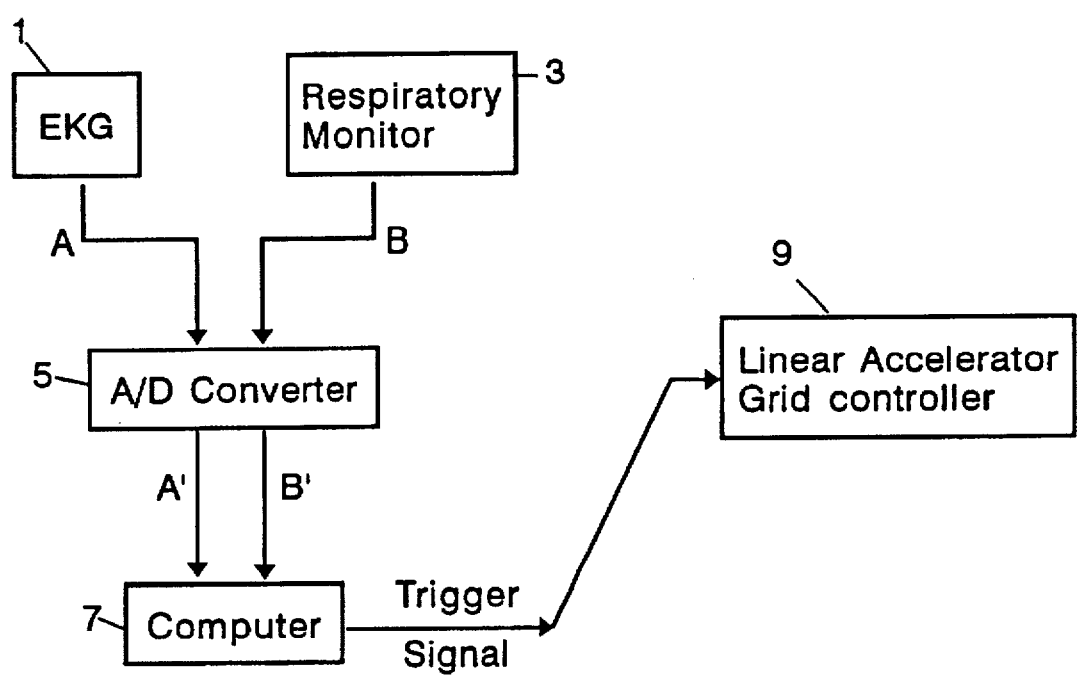
FIG. 1 shows a block diagram of a first embodiment of the instant invention.

According to one aspect of the present invention, a radiation therapy apparatus for applying radiation to a patient in synchronism with one of a plurality of states of a cardiac cycle of a patient and one of a plurality of states of a respiratory cycle of a patient is provided, comprising an electrocardiograph operatively connected to the patient, a respiratory monitor operatively connected to the patient, control means for receiving an output from said electrocardiograph indicative of which of said plurality of cardiac cycle states the cardiac cycle is presently in and for receiving an output from said respiratory monitor indicative of which of said plurality of respiratory cycle states said respiratory cycle is presently in, and radiation application means for applying radiation to the patient in response to a trigger signal from said control means, said trigger signal being generated by said control means in response to said output from said electrocardiograph and said output from said respiratory monitor.

The radiation application means may comprise an x-ray production means for applying x-ray radiation. The x-ray production means may include a linear accelerator. The device may further comprise a linear accelerator grid controller responsive to said trigger signal for controlling said linear accelerator.

The x-ray production means may include a rotating slit collimator. The device may further comprise a motor controller responsive to said trigger signal for controlling said rotating slit collimator.

The control means may comprise a computer. The device may further comprise an analog-to-digital converter connected to said electrocardiograph, said respiratory monitor, and said control means, said analog-to-digital converter being disposed between said electrocardiograph and said control means for converting an analog signal input thereto from the electrocardiograph into a digital signal that is output to said control means and said analog-to-digital converter being disposed between said respiratory monitor and said control means for converting an analog signal input thereto from the respiratory monitor into a digital signal that is output to said control means.

The trigger signal from said control means may be produced in response to the detection by the control means of the occurrence within a predetermined time period of a predetermined one of said plurality of cardiac cycle states and a predetermined one of said plurality of respiratory states.

According to another aspect of the instant invention a radiation therapy apparatus for applying radiation to a patient in synchronism with one of a plurality of states of a cardiac cycle of a patient and one of a plurality of states of a respiratory cycle of a patient is provided, comprising an electrocardiograph operatively connected to the patient, a respiratory monitor operatively connected to the patient, display means for receiving an output from said electrocardiograph for displaying which of said plurality of cardiac cycle states the cardiac cycle was in at a given time and for receiving an output of said respiratory monitor for displaying which of said plurality of respiratory cycle states said respiratory cycle was in at a given time, control means for receiving user input indicative of a selected point or interval of time when a chosen one of said plurality of cardiac cycle states overlaps with a chosen one of said plurality of respiratory cycle states and for outputting a trigger signal at said selected point or interval of time based upon the output from the electrocardiograph input thereto and the output from the respiratory monitor input thereto, and radiation application means for applying radiation to the patient in response to the trigger signal from said control means.

The radiation application means may comprise an x-ray production means for applying x-ray radiation. The x-ray production means may include a linear accelerator. The device may further comprise a linear accelerator grid controller responsive to said trigger signal for controlling said linear accelerator.

The x-ray production means may include a rotating slit collimator. The device may further comprise a motor controller responsive to said trigger signal for controlling said rotating slit collimator.

The control means may comprise a computer. The device may further comprise an analog-to-digital converter connected to said electrocardiograph, said respiratory monitor, and said control means, said analog-to-digital converter being disposed between said electrocardiograph and said control means for converting an analog signal input thereto from the electrocardiograph into a digital signal that is output to said control means and said analog-to-digital converter being disposed between said respiratory monitor and said control means for converting an analog signal input thereto from the respiratory monitor into a digital signal that is output to said control means.

The control means may further comprise storage means for storing a plurality of selected points of time corresponding to a respective plurality of patients, whereby said control means outputs a trigger signal at one of said stored plurality of selected points of time based upon the output from the electrocardiograph input thereto and the output from the respiratory monitor input thereto in response to user input selecting one of said plurality of patients.

According to another aspect of the instant invention a method of applying radiation to a patient in synchronism with one of a plurality of states of a cardiac cycle of a patient and one of a plurality of states of a respiratory cycle of a patient is provided, comprising operatively connecting an electrocardiograph to the patient, operatively connecting a respiratory monitor to the patient, receiving, at a control means, an output from said electrocardiograph indicative of which of said plurality of cardiac cycle states the cardiac cycle is presently in, for receiving, at the control means, an output from said respiratory monitor indicative of which of said plurality of respiratory cycle states said respiratory cycle is presently in, and applying radiation to the patient in response to a trigger signal from said control means, said trigger signal being generated by said control means in response to said output from said electrocardiograph and said output from said respiratory monitor.

According to another aspect of the instant invention a method of applying radiation to a patient in synchronism with one of a plurality of states of a cardiac cycle of a patient and one of a plurality of states of a respiratory cycle of a patient is provided, comprising operatively connecting an electrocardiograph to the patient, operatively connecting a respiratory monitor to the patient, displaying, on a display means, an output from said electrocardiograph indicative of which of said plurality of cardiac cycle states the cardiac cycle was in at a given time, displaying, on the display means, an output from said respiratory monitor indicative of which of said plurality of respiratory cycle states said respiratory cycle was in at a given time, receiving, at a control means, user input indicative of a selected point or interval of time when a chosen one of said plurality of cardiac cycle states overlaps with a chosen one of said plurality of respiratory cycle states, outputting a trigger signal from the control means at said selected point or interval of time based upon the output from the electrocardiograph input to the control means and the output from the respiratory monitor input to the control means, and applying radiation to the patient in response to the trigger signal from said control means.

Referring now to FIG. 1, a block diagram of a first embodiment of the instant invention is shown. As seen in this Fig., electrocardiograph 1, which is operatively connected to a patient (not shown) to measure the patient's cardiac cycle, feeds an analog output signal A indicative of the cardiac cycle to analog-to-digital converter 5. Likewise, respiratory monitor 3, which is operatively connected to the patient (not shown) to measure the patient's respiratory cycle, feeds an analog output signal B indicative of the respiratory cycle to the analog-to-digital converter 5.

The analog-to-digital converter 5 converts analog signal A into digital signal A' and provides the digital signal A' to computer 7. Analog-to-digital converter 5 likewise converts analog signal B into digital signal B' and provides the digital signal B' to computer 7. Computer 7 generates a trigger signal at a point in time that a predetermined state of the cardiac cycle measured by the electrocardiograph 1 overlaps a predetermined state of the respiratory cycle measured by the respiratory monitor 3.

The trigger signal generated by the computer 7 is applied to linear accelerator grid controller 9 to cause a linear accelerator (not shown) that is connected to the linear accelerator grid controller 9 to irradiate the patient (not shown) at a predetermined position.

Figure 2:
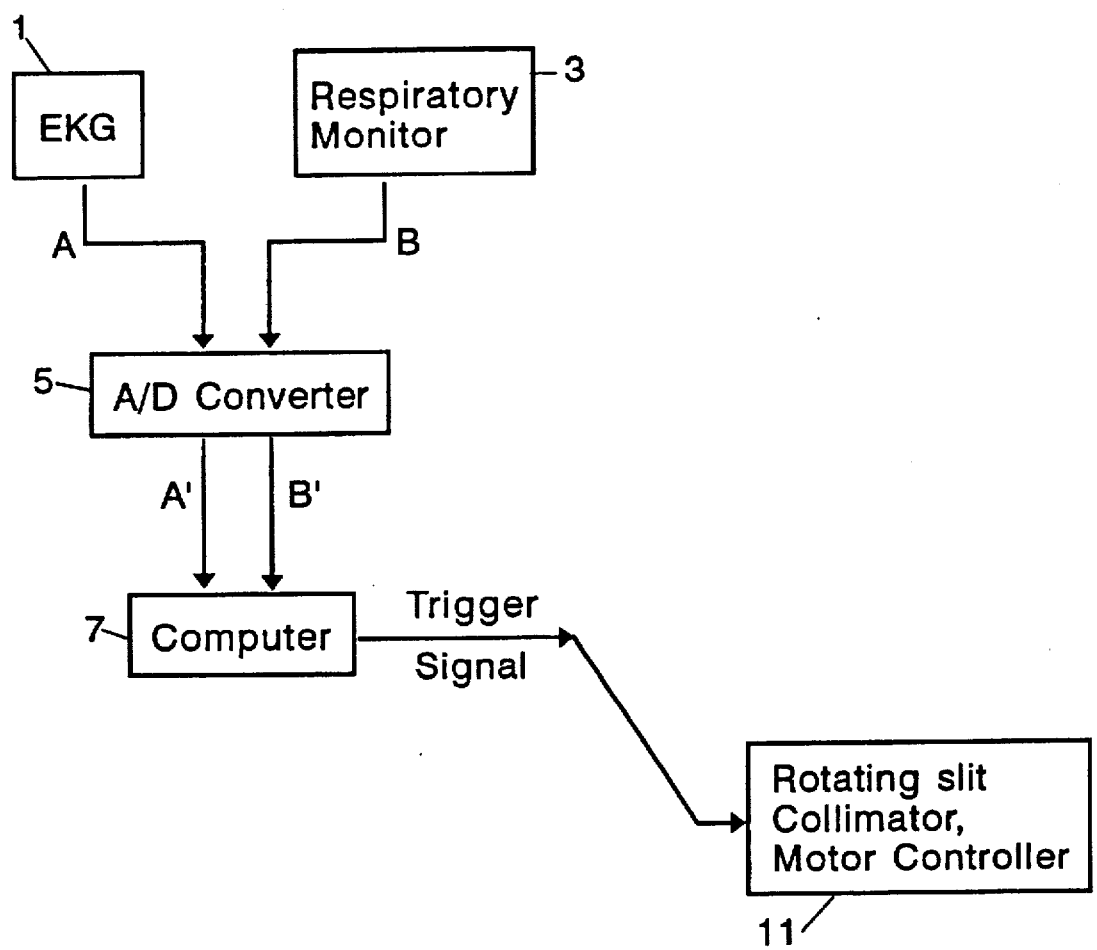
FIG. 2 shows a block diagram of a second embodiment of the instant invention.

Referring now to FIG. 2, in which the same reference numerals of FIG. 1 apply to the same elements and do not require a detailed explanation, a block diagram of a second embodiment of the instant invention is shown.

In this second embodiment of the instant invention the trigger signal output from computer 7 is provided to the motor controller of a rotating slit collimator to selectively irradiate the patient (not shown) at a predetermined position when the trigger signal is received. Of course, the trigger signal could, in the alternative, be applied to a multi-leaf collimator, such as a rotating multi-leaf collimator.

Figure 3:
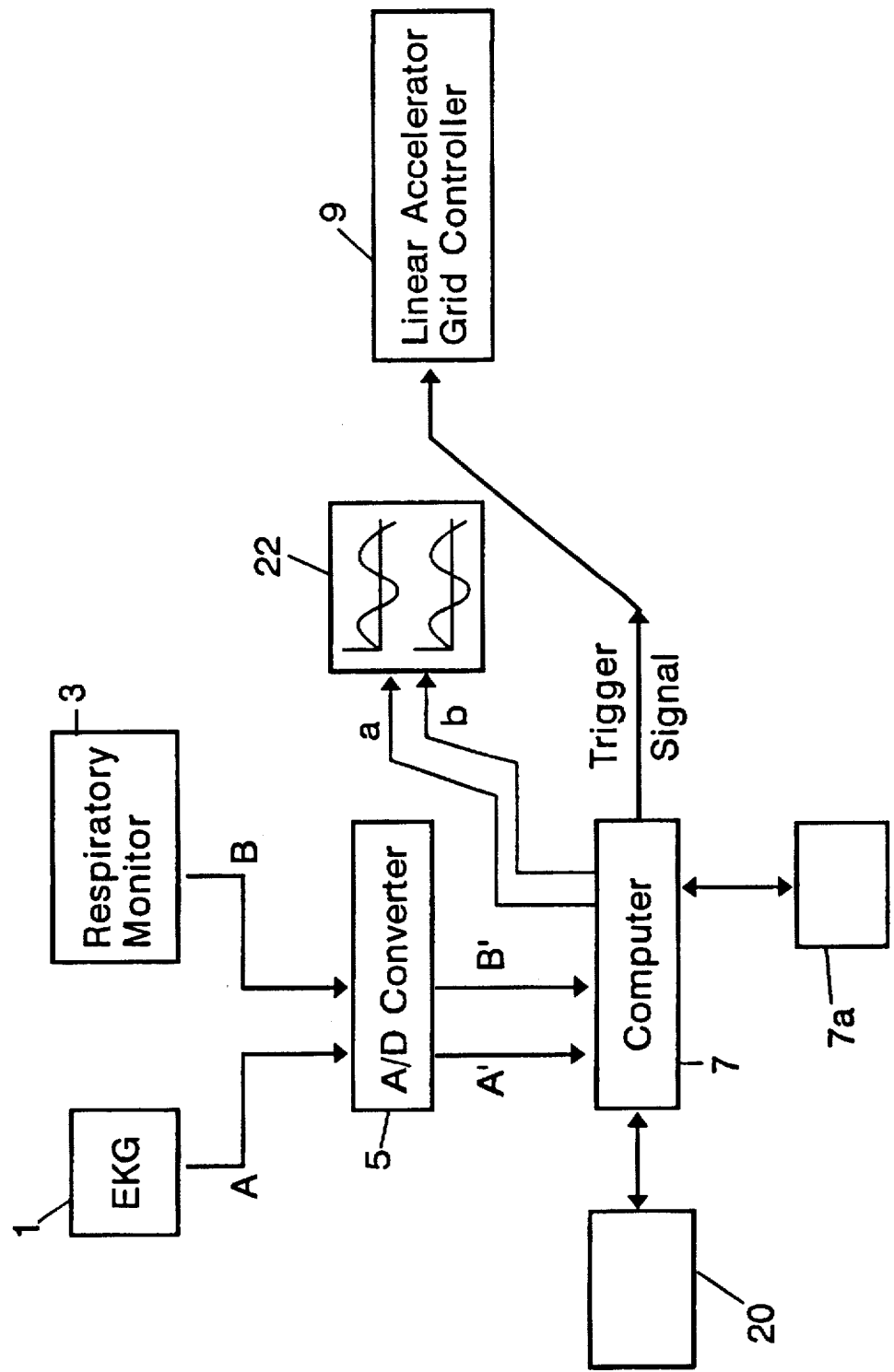
FIG. 3 shows a block diagram of a third embodiment of the instant invention.

Referring now to FIG. 3, in which the same reference numerals of FIG. 1 apply to the same elements and do not require a detailed explanation, a block diagram of a third embodiment of the instant invention is shown.

In this third embodiment of the instant invention a display 22 displays a time-varying plot of the electrocardiograph output (signal a) and a time-varying plot of the respiratory monitor output (signal b). A user input device 20, such as a keyboard or mouse, for example, is operatively connected to computer 7.

A user may use the user input device 20 to select a chosen point in time when a chosen state of the cardiac cycle overlaps with a chosen state of the respiratory cycle, as indicated on the display 22. Computer 7 may include storage element 7a, such as a hard disk drive, floppy drive, or solid-state memory, for example. The storage element 7a may store, for each of a plurality of patients, data indicative of the chosen point in time when a chosen state of the cardiac cycle overlaps with a chosen state of the respiratory cycle.

Referring now to FIG. 4, in which the same reference numerals of FIGS. 2 and 3 apply to the same elements and do not require a detailed explanation, a block diagram of a fourth embodiment of the instant invention is shown.

In this fourth embodiment of the instant invention the trigger signal output from computer 7 is provided to the motor controller of a rotating slit collimator to selectively irradiate the patient (not shown) at a predetermined position when the trigger signal is received.

The instant invention may utilize one or more megavoltage X-ray beams from a conventional linear accelerator or other source to provide a uniform dose coverage of 2–3 cm length of targeted arterial wall. Other sites that move during the cardiac and/or respiratory cycle to which radiation may be applied by the instant invention include, but are not limited to, the heart itself, the mediastinum, the lung, the breast, the kidney, the esophagus, the chest area, the liver, and the peripheral blood vessels. Tumors at these listed sites, as well as other sites, may be treated as may Hodgkins disease. The application of radiation may be synchronized with the passive fill fraction of the cardiac cycle, where heart motion is minimal and arterial localization, for example, is reproducible. Further, radiation may be applied during a specific portion of the cardiac and/or respiratory cycles (for example, during the diastolic or systolic portion of the cardiac cycle) to a site such as a tumor that does not move substantially during the cycle but that is nevertheless affected by the cycle. It must be noted that the instant method and apparatus are useful for radiation therapy, in which application of radiation to the patient performs a therapeutic function, as opposed to diagnosis, in which radiation is applied to perform a diagnostic function.

Externally applied radiation treatments could be used for superficially located hemodialysis shunts. A single electron beam, which may be in the megavolt range, could be tailored to ideally match the desired treatment volume with rapid dose fall-off beyond the field edges and such radiation application may provide a more uniform dose distribution than an intraluminal insertion. Since the shunts are superficial, simple palpation could enable accurate field alignment, even for fractionated treatments.

Conventional fixed beam teletherapy may be utilized to apply the radiation to the patient. In the alternative, Intensity Modulated Radiation Therapy (IMRT) using Dynamic Multileaf Collimators (DMLC) may be used to apply the radiation to the patient.

In particular, IMRT entails rotation of the linear accelerator gantry in coordination with the opening and closing of the DMLC jaws. When delivering IMRT, at any desired combination of gantry angle and DMLC jaw position, the linear accelerator beams can be gated by the inventive method and apparatus to insure that radiation is only applied at the proper time.

It must be noted that although the present invention is described by reference to particular embodiments thereof, many changes and modifications of the invention may become apparent to those skilled in the art without departing from the spirit and scope of the invention as set forth in the claims. For example, a predetermined state or states of only a single one of the cardiac cycle or respiratory cycle may be utilized in the generation of the trigger signal. Further, other radiation producing sources besides those described may, of course, be utilized.

REFERENCES

1. Wiederman J, Marobe C, Amols H, Schwartz A, & Weinberger J, "Intracoronary irradiation markedly reduces restenosis after balloon angioplasty in a porcine model", J. Amer. Col. Card., 23, 1491-8, 1994.
2. Wiederman J, Marobe C, Amols H, Schwartz A, & Weinberger J, "Intracoronary irradiation markedly reduces neointimal proliferation after balloon angioplasty in swine: persistent benefit at 6-month follow-up", J. Amer. Col. Card, 25, 1451-6, 1995.
3. Waksman R, Robinson K. A, Crocker IR, Garvanis MB, Cipolla GD, King SB. "Endovascular low-dose irradiation inhibits neointima formation after coronary artery balloon injury in swine. A possible role for radiation therapy in restenosis prevention", Circulation, 91, 1533-9, 1995.
4. Fischell TA, Abbas MA & Kallman RF, "Low-dose radiation inhibits clonal proliferation of smooth muscle cells: a new approach to restenosis", Arteriosclerosis & Thrombosis, 11, 1435A, 1991.
5. Bottcher HD, Schopohl B, Lierman D, Kollath J & Adamietz IA, "Endovascular irradiation—a new method to avoid recurrent stenosis after stent implantation in peripheral arteries: technique and preliminary results", Int. J. Rad. Onc. Biol. Phys, 29, 183–186, 1994.
6. Schwartz RS, Koval TM, Edwards WD, Camrud AR, Bailey KR, Brown K, Vlietstra RE, & Holmes DR, "Effect of external beam irradiation on neointimal hyperplasia after experimental coronary artery injury", J. Am. Col. Cardiol, 19, 1106–1113, 1992.
7. Abbas MA, Afshari NA & Standius ML et al, "External beam irradiation inhibits neointimal hyperplasia following balloon angioplasty", Cardiol., 44, 191–202, 1994.
8. M. R. Mayberg, Z. Luo, S. Landon, C. Gajdusak, and J. S. Rasey, "Radiation inhibition of intimal hyperplasia after arterial injury", Rad. Res. 142, 212–220 (1995).
9. Gellman, J.; Healey, G.; Qingsheng, C.; Tselentakis, M. J. "The effects of very low dose irradiation on restenosis following balloon angioplasty. A study in the atherosclerotic rabbit." Circulation 84 (suppl. II); 46A–59A (1991).
10. Bentel, G. "Positioning and immobilization of patients undergoing radiation therapy for Hodgkin's disease." Medical Dosimetry 16 (3 1991): 111-7.
11. Daftari, L., P. L. Petti, J. M. Collier, J. R. Castro, and S. Pitluck, "The effect of patient motion on dose uncertainty in charged particle irradiation for lesions encircling the brain stem or spinal cord." Medical Physics 18 (6 1991): 1105–15.
12. Dunscombe, P. B., K. Fox, S. Loose, and K. Leszczynski. "The investigation and rectification of field placement errors in the delivery of complex head and neck fields." International Journal of Radiation Oncology, Biology, Physics 26 (1 1993): 155–61.
13. Dunscombe, P. B., K. Fox, and S. Ryder. "A proposal for the classification of field placement errors in radiotherapy." Medical Dosimetry 16 (1 1991): 1–5.
14. Engler, M. J., B. H. Curran, J. S. Tsai, E. S. Sternick, W. D. Selles, D. E. Wazer, W. P. Mason, T. Sailor, and T. R. Mackie. "Fine tuning of linear accelerator accessories for sterotactic radiotherapy." International Journal of Radiation Oncology, Biology, Physics 28 (4 1994): 1001–8
15. Fishman, E. K. and D. R. Ney. "Advanced computer applications in radiology: clinical applications. [Review]." Radiographics 13 (2 1993): 463–75.
16. Hamlet, S., G. Ezzell, and A. Aref. "Larynx motion associated with swallowing during radiation therapy." International Journal of Radiation Oncology, Biology, Physics 28 (2 1994): 467–70.
17. Moerland, M. A., van, den, Bergh, Ac, R. Bhagwandien, W. M. Janssen, C. J. Bakker, J. J. Lagendijk, and J. J. Battermann. "The influence of respiration induced motion of the kidneys on the accuracy of radiotherapy treatment planning, a magnetic resonance imaging study." Radiotherapy & oncology 30 (2 1994): 150–4.
18. Perez, C. A., J. A. Purdy, W. Harms, R. Gerber, J. Matthews, P. W. Grigsby, M. L. Graham, B. Emami, H. K. Lee, J. M. Michalski, and I. et. "Design of a fully integrated three-dimensional computed tomography simulator and preliminary clinical evaluation." International Journal of Radiation Oncology, Biology, Physics 30 (4 1994): 887–97.
19. Phillips, M. H., E. Pedroni, H. Blattmann, T. Boehringer, A. Corary, and S. Scheib. "The effects of respiratory motion on dose uniformity with a charged particle scanning method." Physics in Medicine & Biology 37 (1 1992):223–34.
20. Scheck, R. J., T. Wendt, and M. Panzer. "Digital storage phosphor radiography for treatment verification in radiotherapy." British Journal of Radiology 66 (789 1993): 801–6.
21. Schwartz, L. H., J. Richard, L. Buffat, E. Touboul, and M. Schlienger. "Kidney mobility during respiration." Radiotherapy & Oncology 32 (1 1994): 84–6.
22. Slifer, K. J., J. D. Bucholtz, and M. D. Cataldo. "Behavioral training of motion control in young childern undergoing radiation treatment without sedation." Journal of Pediatric Oncology Nursing 11 (2 1994): 55–63.
23. Svensson, R., P. Kallman, and A. Brahme. "An analytical solution for the dynamic control of multileaf collimators." Physics in Medicine & Biology 39 (1 1994):37–61.
24. Thornton, Af Jr, Haken Rk Ten, A. Gerhardsson, and M. Correll. "Three-dimensional motion analysis of an improved head immobilization system for simulation, CT, MRI, and PET imaging. [Review]." Radiotherapy & Oncology 20 (4 1991): 224∝8.
25. Zacarias, A. S., R. G. Lane, and L. I. Rosen. "Assessment of a linear accelerator for segmented conformal radiation therapy." Medical Physics 20 (1 1993): 193–8.

What is claimed is:

1. A radiation therapy apparatus for applying radiation to a patient in synchronism with one of a plurality of states of a cardiac cycle of the patient and one of a plurality of states of a respiratory cycle of the patient, comprising:

an electrocardiograph operatively connected to the patient;

a respiratory monitor operatively connected to the patient;

means for interactively receiving user input indicative of a selected point or interval of time when a chosen one of said plurality of cardiac cycle states overlaps with a chosen one of said plurality of respiratory cycle states;

control means supplied with the user input from the means for receiving, an output from said electrocardiograph indicative of which of said plurality of cardiac cycle states the cardiac cycle is presently in, and an output from said respiratory monitor indicative of which of said plurality of respiratory cycle states said respiratory cycle is presently in; and radiation application means for applying radiation to the patient in response to a trigger signal from said control means, said trigger signal being generated by said control means in response to said user input from the means for receiving, said output from said electrocardiograph, and said output from said respiratory monitor.

2. The apparatus of claim 1, wherein said radiation application means comprises an x-ray production means for applying x-ray radiation.

3. The apparatus of claim 2, wherein said x-ray production means includes a linear accelerator.

4. The apparatus of claim 3, further comprising a linear accelerator grid controller responsive to said trigger signal for controlling said linear accelerator.

5. The apparatus of claim 2, wherein said x-ray production means includes a rotating slit collimator.

6. The apparatus of claim 5, further comprising a motor controller responsive to said trigger signal for controlling said rotating slit collimator.

7. The apparatus of claim 1, wherein said control means comprises a computer.

8. The apparatus of claim 7, further comprising an analog-to-digital converter connected to said electrocardiograph, said respiratory monitor, and said control means, said analog-to-digital converter being disposed between said electrocardiograph and said control means for converting an analog signal input thereto from the electrocardiograph into a digital signal that is output to said control means and said analog-to-digital converter being disposed between said respiratory monitor and said control means for converting an analog signal input thereto from the respiratory monitor into a digital signal that is output to said control means.

9. The apparatus of claim 1, wherein said trigger signal from said control means is produced in response to the detection by the control means of the occurrence within a predetermined time period specified by the user input of a predetermined one of said plurality of cardiac cycle states and a predetermined one of said plurality of respiratory cycle states.

10. A radiation therapy apparatus for applying radiation to a patient in synchronism with one of a plurality of states of a cardiac cycle of the patient and one of a plurality of states of a respiratory cycle of the patient, comprising:

an electrocardiograph operatively connected to the patient;

a respiratory monitor operatively connected to the patient;

display means for receiving an output from said electrocardiograph for displaying which of said plurality of cardiac cycle states the cardiac cycle was in at a given time and for receiving an output of said respiratory monitor for displaying which of said plurality of respiratory cycle states said respiratory cycle was at a given time;

means for interactively receiving user input indicative of a selected point or interval of time when a chosen one of said plurality of cardiac cycle states overlaps with a chosen one of said plurality of respiratory cycle states;

control means supplied with the user input from the means for receiving for outputting a trigger signal at said selected point or interval of time based upon the output from the electrocardiograph input thereto and the output from the respiratory monitor input thereto; and radiation application means for applying radiation to the patient in response to the trigger signal from said control means.

11. The apparatus of claim 10, wherein said radiation application means comprises an x-ray production means for applying x-ray radiation.

12. The apparatus of claim 11, wherein said x-ray production means includes a linear accelerator.

13. The apparatus of claim 12, further comprising a linear accelerator grid controller responsive to said trigger signal for controlling said linear accelerator.

14. The apparatus of claim 11, wherein said x-ray production means includes a rotating slit collimator.

15. The apparatus of claim 14, further comprising a motor controller responsive to said trigger signal for controlling said rotating slit collimator.

16. The apparatus of claim 10, wherein said control means comprises a computer.

17. The apparatus of claim 16, further comprising an analog-to-digital converter connected to said electrocardiograph, said respiratory monitor, and said control means, said analog-to-digital converter being disposed between said electrocardiograph and said control means for converting an analog signal input thereto from the electrocardiograph into a digital signal that is output to said control means and said analog-to-digital converter being disposed between said respiratory monitor and said control means for converting an analog signal input thereto from the respiratory monitor into a digital signal that is output to said control means.

18. The apparatus of claim 10, wherein said control means further comprises storage means for storing a plurality of selected points of time corresponding to a respective plurality of patients, whereby said plurality of selected points of time are received by said control means through said means for receiving user input, and whereby said control means outputs a trigger signal at one of said stored plurality of selected points of time based upon the output from the electrocardiograph input thereto in response to user input selecting one of said plurality of patients.

19. A method of applying radiation to a patient in synchronism with one of a plurality of states of a cardiac cycle of the patient and one of a plurality of states of a respiratory cycle of the patient, comprising;

operatively connecting an electrocardiograph to the patient;

operatively connecting a respiratory monitor to the patient;

interactively receiving, at means for receiving user input, user input indicative of a selected point or interval of time when a chosen one of said plurality of cardiac cycle states overlaps with a chosen one of said plurality of respiratory cycle states;

receiving, at control means supplied with said user input, an output from said electrocardiograph indicative of which of said plurality of cardiac cycle states the cardiac cycle is presently in and receiving, at the control means, an output from said respiratory monitor indicative of which of said plurality of respiratory cycle states said respiratory cycle is presently; and applying radiation to the patient in response to a trigger signal from said control means, said trigger signal being generated by said control means in response to said user input, said output from said electrocardiograph, and said output from said respiratory monitor.

20. A method of applying radiation to a patient in synchronism with one of a plurality of states of a cardiac cycle of the patient and one of a plurality of states of a respiratory cycle of the patient, comprising:

operatively connecting an electrocardiograph to the patient;

operatively connecting a respiratory monitor to the patient;

displaying, on display means, an output from said electrocardiograph indicative of which of said plurality of cardiac cycle states the cardiac cycle was in at a given time and displaying, on the display means, an output from said respiratory monitor indicative of which of said plurality of respiratory cycle states said respiratory cycle was in at a given time;

interactively receiving, at means for receiving user input, user input indicative of a selected point or interval of time when a chosen one of said plurality of cardiac cycle states overlaps with a chosen one of said Plurality of respirator cycle states;

receiving, at control means, the user input and outputting a trigger signal from the control means at said selected point or interval of time based upon the output from the electrocardiograph input to the control means and the output from the respiratory monitor input to the control means; and applying radiation to the patient in response to the trigger signal from said control means.

* * * * *